US006967107B2

(12) United States Patent
Buechler et al.

(10) Patent No.: US 6,967,107 B2
(45) Date of Patent: Nov. 22, 2005

(54) N-ARYL-CARBAMIC ACID ESTER-DERIVED AND VALERIC ACID ESTER-DERIVED CROSS-LINKERS AND CONJUGATES, AND METHODS FOR THEIR SYNTHESIS AND USE

(75) Inventors: Kenneth F. Buechler, San Diego, CA (US); Mariusz G. Banaszczyk, San Marcos, CA (US); Joseph Barry Noar, Solana Beach, CA (US)

(73) Assignee: Biosite, Inc., San Diego, CA (US)

( * ) Notice: Subject to any disclaimer, the term of this patent is extended or adjusted under 35 U.S.C. 154(b) by 0 days.

(21) Appl. No.: 11/080,211

(22) Filed: Mar. 14, 2005

(65) Prior Publication Data

US 2005/0181416 A1    Aug. 18, 2005

Related U.S. Application Data

(62) Division of application No. 10/778,919, filed on Feb. 12, 2004, now Pat. No. 6,887,952.

(51) Int. Cl.$^7$ .................. G01N 33/547; G01N 33/532; C07D 207/22; C07D 207/30; C07L 89/00
(52) U.S. Cl. ..................... 436/533; 436/532; 436/543; 525/54.1; 525/532; 548/534; 548/545; 548/563
(58) Field of Search ............................... 436/533, 532, 436/543; 525/532, 54.1; 548/534, 545, 563

(56) References Cited

U.S. PATENT DOCUMENTS

| 5,643,575 | A  | 7/1997 | Martinez et al. |
| 5,672,662 | A  | 9/1997 | Harris et al. |
| 5,705,153 | A  | 1/1998 | Shorr et al. |
| 5,730,990 | A  | 3/1998 | Greenwald et al. |
| 5,763,189 | A  | 6/1998 | Buechler et al. |
| 5,902,588 | A  | 5/1999 | Greenwald et al. |
| 5,932,462 | A  | 8/1999 | Harris et al. |
| 6,238,931 | B1 | 5/2001 | Buechler et al. |
| 6,251,687 | B1 | 6/2001 | Buechler et al. |

FOREIGN PATENT DOCUMENTS

WO    WO 95/08772    3/1995

OTHER PUBLICATIONS

Gibson et al., "Nonpeptidic $\alpha_{84}\beta_3$ Integrin Antagonist Libraries: On-Bead Screening and Mass Spectrometric Identification without Tagging," Agnew. Chem. Int. Ed. 40: 165-169, 2001.

Gottschling et al., "Cellular Solid-Phase Binding Assay and Mass Spectrometry for Screening of $\alpha 4\beta 7$ Integrin Antagonists," Bioorg. Med. Chem. Lett. 11:2997-3000, 2001.

Leon et al., "Evaluation of Resins for On-Bead Screening: A Study of Papain and Chymotrypsin Specificity Using Pega-Bound Combinatorial Peptide Libraries," Bioorg. Med. Chem. Lett. 8:2997-3002, 1998.

Orain and Bradley, "Solid Phase synthesis of tyrpanothione reductase inhibitors—towards single bead screening," Tetrahedron Lett. 42:515-518, 2001.

Papanikos et al., "$\alpha$-Ketocarbonyl Peptides: A General Approach to Reactive Resin-Bound Intermediates in the Synthesis of Peptide Isosteres for Protease Inhibitor Screening on Solid Support," J. Am. Chem. Soc. 123:2176-2181, 2001.

Smith and Bradley, "comparison of Resin and Solution Screening Methodologies in Combinatorial Chemistry and the Identification of a 100 nM Inhibitor of Trypanothione Reductases," J. Comb. Med. 1:326-332, 1999.

Topchieva et al., "Synthesis and Physiochemical Properties of Protein Conjugates with Water-Soluble Poly(alkylene oxides)," Bioconjung. Chem. 6:380-8, 1995.

Ward et al., "Binding activities of a repertoire of single immunoglobulin variable domins secreted from *Escherichia coli*," Nature 341:544-546, 1989.

Wilson, "Simplified conjugation chemistry for coupling peptides to F(ab') fragments: autologous red cell agglutination assay for HIV-1 antibodies," J. Immunol. Methods 175:267-273; 1994.

Yarmush, "coupling of antibody-binding fragments to solid-phase supports: site-directed ,binding of F(ab)$_2$ fragments," J. Biochem. Biophys. Methods 25:85-97, 1992.

*Primary Examiner*—Long V. Le
*Assistant Examiner*—Shafiqul Haq
(74) *Attorney, Agent, or Firm*—Foley & Lardner LLP

(57) ABSTRACT

The present invention describes carbamic acid ester-derived and valeric acid ester-derived polyfunctional cross-linker molecules, and methods for their synthesis and use. The inclusion of polymeric moieties such as poly(alkylene oxide) in the cross-linkers of the present invention can provide advantageous solubility properties in aqueous environments. Such cross-linkers may be used to form conjugates for use in a variety of assay formats.

16 Claims, No Drawings

N-ARYL-CARBAMIC ACID ESTER-DERIVED AND VALERIC ACID ESTER-DERIVED CROSS-LINKERS AND CONJUGATES, AND METHODS FOR THEIR SYNTHESIS AND USE

CROSS-REFERENCE TO RELATED PATENT APPLICATIONS

This application is a Division of U.S. application Ser. No. 10/778,919, filed Feb. 12, 2004 now U.S. Pat. No. 6,887,952, incorporated herein by reference in its entirety.

FIELD OF THE INVENTION

The present invention relates to novel carbamic acid and valeric acid esters useful as cross-linkers, to conjugates comprising such cross-linkers, and to methods for their synthesis and use.

BACKGROUND OF THE INVENTION

The following discussion of the background of the invention is merely provided to aid the reader in understanding the invention and is not admitted to describe or constitute prior art to the present invention.

Chemical cross-linkers are valuable tools for scientists and are discussed in numerous books and catalogues. See, e.g., Wong, *Chemistry of Protein Conjugation and Cross-linking*, CRC Press, Boca Raton, Fla., 1991. These reagents may be used in a variety of ways, such as to assist in the determination of near-neighbor relationships in proteins, molecular associations in cell membranes, three-dimensional structures of proteins, enzyme-substrate orientation, solid-phase immobilization, and hapten-carrier protein conjugation. They are also useful for preparing antibody-detectable label conjugates, immunotoxins and other labeled protein and nucleic acid reagents. Cross-linking agents often employ functional groups that couple to amino acid side chains of peptides. These reagents may be classified on the basis of the following:

1. Functional groups and chemical specificity;
2. length and composition of the cross-bridge;
3. whether the cross-linking groups are similar (homobifunctional) or different (heterobifunctional);
4. whether the groups react chemically or photochemically;
5. whether the reagent is cleavable; and
6. whether the reagent can be radiolabeled or tagged with another label.

Reactive groups that can be targeted using a cross-linker include primary amines, sulfhydryls, carbonyls, carbohydrates and carboxylic acids. In addition, many reactive groups can be coupled nonselectively using a cross-linker such as photoreactive phenyl azides.

Cross-linking reagents contain at least two reactive groups, and are divided generally into homofunctional cross-linkers (containing identical reactive groups) and heterofunctional cross-linkers (containing non-identical reactive groups). While for convenience the following discussion refers to homobifunctional and heterobifunctional cross-linkers (where "bifunctional" refers to the presence of two functional groups), cross-linking reagents having more than two functional groups are well known to the artisan and are within the scope of the invention described herein.

Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. These cross-linkers can penetrate cell membranes and cross-link proteins within the membrane to study membrane composition, structure and protein-protein and protein-lipid interactions. Imidoesters are also useful for oligomer formation. For example, cross-linking proteins to form oligomers may reveal if a bivalent, dimeric or trimeric form of the protein is responsible for activity.

A nonselective homobifunctional cross-linker is useful for conjugating functional groups, such as hydroxyls for which specific cross-linkers are not available. An example of a nonselective homobifunctional cross-linker is BASED (Product #21564 Pierce Co.). This cross-linker has a long spacer arm and 2 aromatic rings which makes it very hydrophobic with a limited solubility in aqueous systems. This cross-linker also has a large diffusion capacity and may be useful for permeation of biological membranes before conjugation initiates.

Heterobifunctional cross-linkers possess two or more different reactive groups that allow for sequential conjugations with specific groups of proteins, minimizing undesirable polymerization or self-conjugation. Heterobifunctional reagents are also used when modification of amines is problematic. Amines may sometimes be found at the active sites of macromolecules, and the modification of these may lead to the loss of activity. Other moieties such as sulfhydryls, carboxyls, phenols and carbohydrates may be more appropriate targets. A two-step strategy allows for the coupling of a protein that can tolerate the modification of its amines to a protein with other accessible groups. A variety of heterobifunctional cross-linkers, each combining different attributes for successful conjugation are commercially available. Cross-linkers that are amine-reactive at one end and sulfhydryl-reactive at the other end are quite common.

If using heterobifunctional reagents, the most labile group is typically reacted first to ensure effective cross-linking and avoid unwanted polymerization. A selection of heterobifunctional reagents that contain at least one photoaffinity group are also commercially available. This selection includes iodinatable and cleavable reagents that react nonspecifically at the azido group and with amines, sulfhydryls, carbohydrates and carbonyls.

Many factors must be considered to determine optimum cross-linker-to-target molar ratios. Depending on the application, the degree of conjugation is an important factor. For example, when preparing immunogen conjugates, a high degree of conjugation is normally desired to increase the immunogenicity of the antigen. However, when conjugating to an antibody or an enzyme, a low-to-moderate degree of conjugation may be optimal to ensure that the biological activity of the protein is retained. It is also important to consider the number of reactive groups on the surface of the protein. If there are numerous target groups, a lower cross-linker-to-protein ratio can be used. For a limited number of potential targets, a higher cross-linker-to-protein ratio may be required. This translates into more cross-linker per gram for a small molecular weight protein.

Conformational changes of proteins associated with a particular interaction may also be analyzed by performing cross-linking studies before and after the interaction. A comparison is made by using different arm-length crosslinkers and analyzing the success of conjugation. The use of cross-linkers with different reactive groups and/or spacer arms may be desirable when the conformation of the protein changes such that hindered amino acids become available for cross-linking.

Cross-linkers are available with varying lengths of spacer arms or bridges connecting the reactive ends. The most apparent attribute of the bridge is its ability to deal with steric considerations of the moieties to be linked. Because steric effects dictate the distance between potential reaction sites for cross-linking, different lengths of bridges may be considered for the interaction. Shorter spacer arms are often used in intramolecular cross-linking studies, while intermolecular cross-linking is favored with a cross-linker containing a longer spacer arm.

The inclusion of polymer portions (e.g., polyethylene glycol ("PEG") homopolymers, polypropylene glycol homopolymers, other alkyl-polyethylene oxides, bis-polyethylene oxides and co-polymers or block co-polymers of poly(alkylene oxides)) in cross-linkers can, under certain circumstances be advantageous. See, e.g., U.S. Pat. Nos. 5,643,575, 5,672,662, 5,705,153, 5,730,990, 5,902,588, and 5,932,462; and Topchieva et al., Bioconjug. Chem. 6: 380–8, 1995). For example, U.S. Pat. No. 5,672,662 discloses bifunctional cross-linkers comprising a PEG polymer portion and a single ester linkage. Such molecules are said to provide a half-life of about 10 to 25 minutes in water.

Each reference cited in the preceding section is hereby incorporated by reference in its entirety, including all tables, figures, and claims.

BRIEF SUMMARY OF THE INVENTION

It is an object of the invention to provide N-aryl-carbamic acid ester derived cross-linkers, and methods of their synthesis and use. In a first aspect, the invention relates to cross-linkers having the general formula:

A—B—C—D where A is a first functional moiety directly or indirectly covalently linked to one terminus of a polymeric moiety C through an N-aryl (or heteroaryl) carbamic acid ester B, and a second functional moiety D directly or indirectly covalently linked to a second terminus of the polymeric moiety C. The first functional moiety A may be linked to the aryl (or heteroaryl) portion of the N-aryl carbamic acid ester via the ortho, meta, or para position relative to the polymeric moiety C. In addition, the aryl (or heteroaryl) portion of the N-aryl carbamic acid ester may be further substituted by one or more additional moieties.

Such cross-linkers, which may be homobifunctional or heterobifunctional, advantageously provide simplified synthetic routes and the ability to monitor synthesis due to the light absorptive properties of the aryl portion of the N-aryl carbamic acid ester. In addition, the polymeric moiety can impart sufficient water solubility to the cross-linkers to compensate for the relatively hydrophobic character of the N-aryl carbamic acid ester portion of the molecule resulting from the presence of the aryl group.

In preferred embodiments, the linker connecting second functional moiety D to the polymeric moiety is a second aryl (or heteroaryl)-containing ester linkage. In these preferred embodiments, second functional moiety D may be linked to this aryl (or heteroaryl) portion of the linker in the ortho, meta, or para position relative to the polymeric moiety C. In addition, the aryl (or heteroaryl) portion of the linker may be substituted by one or more additional moieties.

As is well understood in the art, the functional moieties selected depend upon the group being targeted for attachment of the crosslinker. Preferred functional moieties include primary amine-reactive moieties, sulfhydryl-reactive moieties, nonselective moieties, photoreactive moieties, carboxyl-reactive moieties, arginine-reactive moieties, and carbonyl-reactive moieties. Specific examples of these moieties are described hereinafter.

The polymeric moieties that may find use in the present invention include polyalkylene oxides, including homopolymers and copolymers comprising methylene oxide, ethylene oxide, propylene oxide, isopropylene oxide, and butylene oxide. Additional examples of polymeric moieties are described below. Particularly preferred are polyethylene oxides (i.e., (—CH$_2$CH$_2$O—) n), which are often referred to in the art as PEGs due to their derivation from polyethylene glycol. Preferably, n=from about 40 to about 450 (i.e., the polymeric moieties comprise from about 40 to about 450 monomer units). Preferred cross-linkers have between about 50 and about 150 monomer units, more preferably between about 60 and about 100 monomer units, still more preferably between about 70 and about 90 monomer units, and most preferably about 77 monomer units. The term "about" in this context refers to +/−10% of a given measurement.

The skilled artisan will understand that the commercially available polyalkylene glycol molecules used in the synthesis of the cross-linkers of the present invention are often not pure, and instead are provided as a pool of molecules differing in the number of monomeric units, but having a specified "average molecular weight" as that term is defined hereinafter. Thus, the present invention also relates to compositions comprising a plurality of cross-linkers described herein that may differ in molecular weight (e.g., due to differences in the number of monomeric units in the molymeric moiety), but which comprise polymeric moieties having an average number of monomer units of between about 40 to about 450. The term "about" in this context refers to +/−10% of a given measurement. Preferred compositions comprise cross-linkers having an average number of monomer units of between about 60 and about 100, more preferably between about 70 and about 90, and most preferably about 77.

In certain preferred embodiments, the N-aryl-carbamic acid ester derived cross-linkers of the present invention have the following formula:

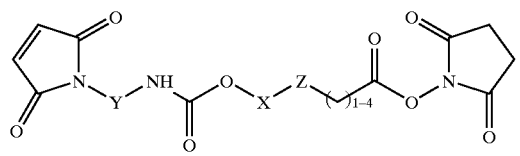

wherein X is (alkylene oxide)$_n$;

n is between about 40 to about 450; and

Y and Z are independently arylene or heteroarylene units having 5 or 6 ring atoms, optionally substituted with from 1 to 4 substituents independently selected from the group consisting of C$_{1-6}$ alkyl straight or branched chain, halogen, trihalomethyl, C$_{1-6}$ alkoxy, —NO$_2$, —NH$_2$, —OH, —COOR', where R' is H or lower alkyl, —CH$_2$OH, —CONH$_2$, and a linkage to a poly(alkylene oxide) moiety, wherein Z is optionally present.

More preferred N-aryl-carbamic acid ester derived cross-linkers of the present invention have the following formula:

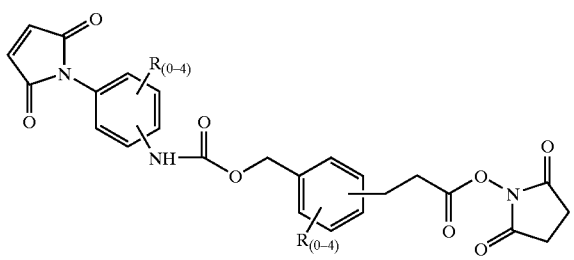

wherein X is (alkylene oxide)$_n$;

n is between about 40 to about 450; and each R is independently selected from the group consisting of $C_{1-6}$ alkyl straight or branched chain, halogen, trihalomethyl, $C_{1-6}$ alkoxy, —NO$_2$, —NH$_2$, —OH, —COOR', where R' is H or lower alkyl, —CH$_2$OH, —CONH$_2$, and a linkage to a poly(alkylene oxide) moiety.

Particularly preferred N-aryl-carbamic acid ester derived cross-linkers of the present invention have the following formula:

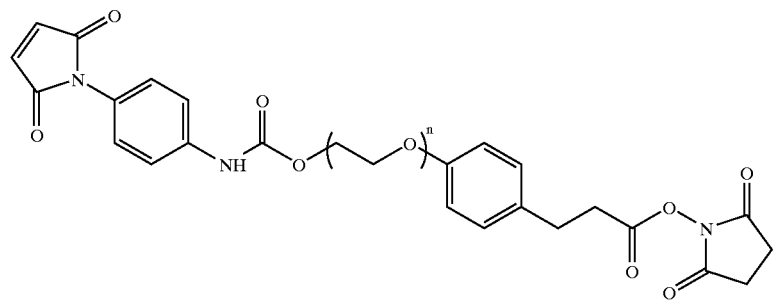

wherein n is between about 40 to about 450.

As described herein, the N-aryl-carbamic acid ester derived cross-linkers of the present invention find use in forming a covalent linkage between two species, such as between a first and second protein, polypeptide, nucleic acid, small molecule, aptamer, carbohydrate, or peptidomimetic; between a protein, polypeptide, nucleic acid, small molecule, aptamer, carbohydrate, peptidomimetic, etc., and a detectable label; between a hapten and a protein or polypeptide acting as an antigenic carrier; and/or between a protein, polypeptide, nucleic acid, small molecule, aptamer, carbohydrate, peptidomimetic, etc., and a solid phase.

In another aspect, then, the present invention provides conjugates formed by the foregoing cross-linker molecules and compositions. Such conjugates have the following general formula:

E—B—C—F where E is a first protein, polypeptide, nucleic acid, small molecule, aptamer, carbohydrate, peptidomimetic, detectable label, or solid phase directly or indirectly covalently linked to one terminus of a polymeric moiety C through an N-aryl (or heteroaryl) carbamic acid ester B, and a second protein, polypeptide, nucleic acid, small molecule, aptamer, carbohydrate, peptidomimetic, detectable label, or solid phase F directly or indirectly covalently linked to a second terminus of the polymeric moiety C. As discussed above, the linkage between E and the aryl (or heteroaryl) portion of the N-aryl carbamic acid ester may be made via the ortho, meta, or para position relative to the polymeric moiety C. In addition, the aryl (or heteroaryl) portion of the N-aryl carbamic acid ester may be further substituted by one or more additional moieties.

In certain preferred embodiments, the conjugates of the present invention have the following formula:

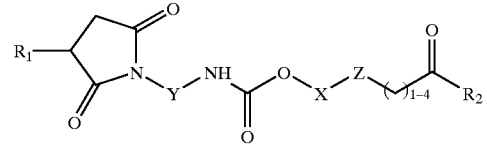

wherein X is (alkylene oxide)$_n$;

n is between about 40 to about 450;

Y and Z are independently arylene or heteroarylene units having 5 or 6 ring atoms, optionally substituted with from 1 to 4 substituents independently selected from the group consisting of $C_{1-6}$ alkyl straight or branched chain, halogen, trihalomethyl, $C_{1-6}$ alkoxy, —NO$_2$, —NH$_2$, —OH, —COOR', where R' is H or lower alkyl, —CH$_2$OH, —CONH$_2$, and a linkage to a poly(alkylene oxide) moiety, wherein Z is optionally present; and R$_1$ and R$_2$ are independently covalent linkages to a protein, polypeptide, signal development element, or solid phase.

In more preferred embodiments, the conjugates of the present invention have the following formula:

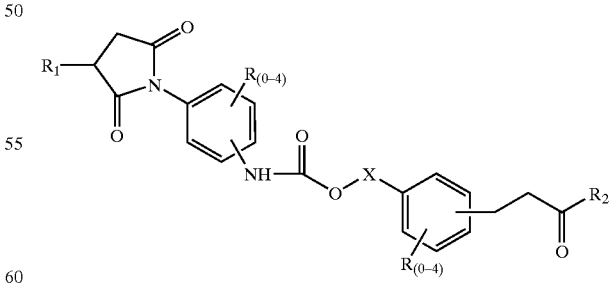

wherein X is (alkylene oxide)$_n$;

n is between about 40 to about 450; and each R is independently selected from the group consisting of $C_{1-6}$ alkyl straight or branched chain, halogen, trihalomethyl, $C_{1-6}$ alkoxy, —NO$_2$, —NH$_2$, —OH, —COOR', where R' is H or lower alkyl, —CH$_2$OH, —CONH$_2$, and a linkage to a poly(alkylene oxide) moiety; and R$_1$ and R$_2$ are independently covalent linkages to a protein, polypeptide, signal development element, or solid phase.

In certain particularly preferred embodiments, the conjugates of the present invention have the following formula:

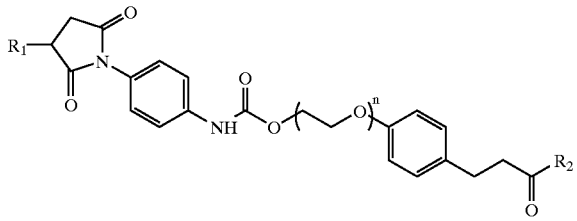

wherein n is between about 40 to about 450; and

R$_1$ and R$_2$ are independently covalent linkages to a protein, polypeptide, signal development element, or solid phase.

Preferably, one of R$_1$ or R$_2$ is selected from the group consisting of a protein, a polypeptide, an antibody, an antibody fragment, a single-chain variable region fragment, a small molecule, a nucleic acid, an oligosaccharide, a polysaccharide, a cyclic polypeptide, a peptidomimetic, and an aptamer; and the other of R$_1$ or R$_2$ is selected from the group consisting of a detectable label and a solid phase. Such conjugates are particularly useful in receptor binding assays. Thus, in another aspect, the present invention relates to receptor binding assays in which the conjugates of the present invention are used. Preferred assay methods include immunoassay, (e.g., competitive assays, non-competitive assays, sandwich assays, homogenous assays, etc.) and nucleic acid hybridization. Examples of such assays are described hereinafter.

It is another object of the present invention to provide valeric acid ester derived cross-linkers, and methods of their synthesis and use. In various aspects, the invention relates to cross-linkers having the general formula:

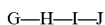

where G is a first functional moiety directly or indirectly covalently linked to one terminus of a polymeric moiety H, and a second functional moiety J covalently linked to a second terminus of the polymeric moiety H through a valeric acid moiety I.

As discussed above, the functional moieties selected depend upon the group being targeted for attachment of the crosslinker, and the resulting crosslinker may be homobifunctional or heterobifunctional. Preferred functional moieties include those described for the foregoing N-aryl-carbamic acid ester derived cross-linkers. Likewise, as discussed above, the polymeric moieties that may find use in the present invention include polyalkylene oxides, including homopolymers and copolymers comprising methylene oxide, ethylene oxide, propylene oxide, isopropylene oxide, and butylene oxide. Particularly preferred are polyethylene oxides. Preferably, the polymeric moieties comprise from about 40 to about 450 monomer units. Preferred cross-linkers have between about 60 and about 90 monomer units, more preferably between about 70 and about 80 monomer units, and most preferably about 77 monomer units.

In certain preferred embodiments, the valeric acid ester derived crosslinkers of the present invention have the following formula:

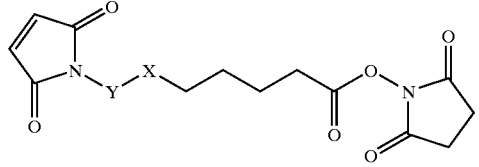

wherein X is (alkylene oxide)$_n$;

n is between about 40 to about 450; and

Y is C$_{1-10}$ alkylene straight or branched chain comprising from 0–4 backbone (i.e., non-substituent) heteroatoms, optionally substituted with from 1 to 4 substituents independently selected from the group consisting of C$_{1-6}$ alkyl straight or branched chain, halogen, trihalomethyl, C$_{1-6}$ alkoxy, —NO$_2$, —NH$_2$, =O, —OH, —CH$_2$OH, —C(O)NH$_2$, and a linkage to a polyalkylene oxide moiety.

More preferred valeric acid ester derived cross-linkers of the present invention have the following formula:

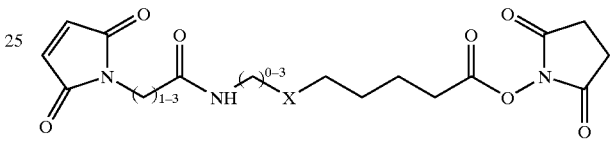

wherein X is (alkylene oxide)$_n$, and n is between about 40 to about 450.

Particularly preferred valeric acid ester derived cross-linkers of the present invention have the following formula:

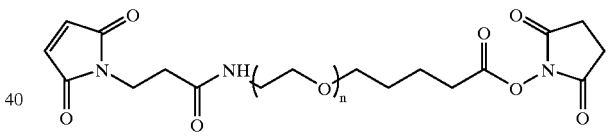

wherein n is between about 40 to about 450.

As in the case of the N-aryl-carbamic acid ester derived cross-linkers, the valeric acid ester derived cross-linkers of the present invention find use in forming a covalent linkage between two species, such as between a first and second protein, polypeptide, nucleic acid, small molecule, aptamer, carbohydrate, or peptidomimetic; between a protein, polypeptide, nucleic acid, small molecule, aptamer, carbohydrate, peptidomimetic, etc., and a detectable label; between a hapten and a protein or polypeptide acting as an antigenic carrier; and/or between a protein, polypeptide, nucleic acid, small molecule, aptamer, carbohydrate, peptidomimetic, etc., and a solid phase.

In another aspect, then, the present invention relates to conjugates formed by the foregoing cross-linker molecules and compositions. Such conjugates have the following general formula:

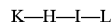

where K is a first protein, polypeptide, nucleic acid, small molecule, aptamer, carbohydrate, peptidomimetic, detectable label, or solid phase directly or indirectly covalently linked to one terminus of a polymeric moiety H, and L is a second protein, polypeptide, nucleic acid, small molecule, aptamer, carbohydrate, peptidomimetic, detectable label, or solid phase covalently linked to a second terminus of the polymeric moiety H through a valeric acid moiety I.

In certain preferred embodiments, the conjugates of the present invention have the following formula:

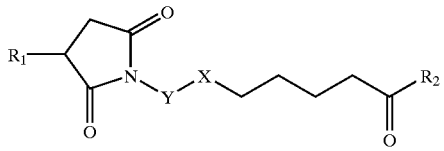

wherein X is (alkylene oxide)$_n$;
n is between about 40 to about 450;
Y is $C_{1-10}$ alkylene straight or branched chain comprising from 0–4 backbone heteroatoms, optionally substituted with from 1 to 4 substituents independently selected from the group consisting of $C_{1-6}$ alkyl straight or branched chain, halogen, trihalomethyl, $C_{1-6}$ alkoxy, —NO$_2$, —NH$_2$, =O, —OH, —CH$_2$OH, —C(O)NH$_2$, and a linkage to a polyalkylene oxide moiety; and
$R_1$ and $R_2$ are independently covalent linkages to a protein, polypeptide, signal development element, or solid phase.

In more preferred embodiments, the conjugates of the present invention have the following formula:

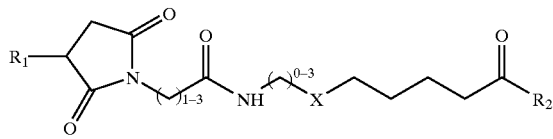

wherein X is (alkylene oxide)$_n$;
n is between about 40 to about 450; and
$R_1$ and $R_2$ are independently covalent linkages to a protein, polypeptide, signal development element, or solid phase.

In particularly preferred embodiments, the conjugates of the present invention have the following formula:

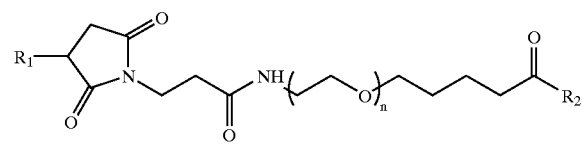

wherein n is between about 40 to about 450; and
$R_1$ and $R_2$ are independently covalent linkages to a protein, polypeptide, signal development element, or solid phase.

Preferably, one of $R_1$ or $R_2$ is selected from the group consisting of a protein, a polypeptide, an antibody, an antibody fragment, a single-chain variable region fragment, a small molecule, a nucleic acid, an oligosaccharide, a polysaccharide, a cyclic polypeptide, a peptidomimetic, and an aptamer; and the other of $R_1$ or $R_2$ is selected from the group consisting of a detectable label and a solid phase. Such conjugates are particularly useful in receptor binding assays. Thus, in another aspect, the present invention relates to receptor binding assays in which the conjugates of the present invention are used. Preferred assay methods include immunoassay, (e.g., competitive assays, non-competitive assays, sandwich assays, homogenous assays, etc.) and nucleic acid hybridization. Examples of such assays are described hereinafter.

It is another object of the present invention to provide assays and devices for performing assays. Such assays and devices comprise a conjugate as described herein comprising an antibody or binding fragment thereof covalently linked to a detectable label; and/or a conjugate as described herein comprising an antibody or binding fragment thereof covalently linked to a solid phase. The devices of the present invention preferably contain a plurality of diagnostic zones, each of which is related to a particular analyte of interest. Such devices may be referred to as "arrays" or "microarrays." Following reaction of a sample with the devices, a signal may be generated from the diagnostic zone(s), which may then be correlated to the presence or amount of the analyte(s) of interest. Numerous suitable devices are known to those of skill in the art, and exemplary devices are described hereinafter.

It is another object of the present invention to provide methods for producing the cross-linker molecules and compositions of the present invention, and methods for producing conjugates using the cross-linker molecules and compositions described herein.

DETAILED DESCRIPTION OF THE INVENTION

The present invention relates to N-aryl carbamic acid ester derived crosslinkers and methods and for their production and use.

N-aryl Carbamic Acid Esters

N-aryl carbamic acid esters (see, e.g., U.S. Pat. No. 3,915,984) have the general formula:

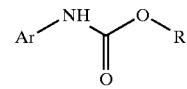

While Ar is most preferably a monocyclic carbocyclic aromatic ring having 5 or 6 ring atoms (and is most preferably phenyl), the aryl or heteroaryl Ar group (formed into an arylene or heteroarylene in the crosslinkers described herein by elaboration from a ring atom) generally may contain up to ten ring atoms, although the skilled artisan will recognize that Ar groups with more than ten ring atoms are within the scope of the invention. Ar can be a monocyclic or fused bicyclic aryl, alkaryl, heteroaryl or heteroarylalkyl group. The ring systems encompassed by Ar can contain up to four heteroatoms, independently selected from the group consisting of N, S, and O. When Ar is a heteroaryl ring or ring system, it preferably contains one or two heteroatoms.

Monocyclic Ar groups include, but are not limited to: phenyl, thiazoyl, furyl, pyranyl, 2H-pyrrolyl, thienyl, pyrroyl, imidazoyl, pyrazoyl, pyridyl, pyrazinyl, pyrimidinyl, and pyridazinyl moieties. Fused bicyclic Ar groups include, but are not limited to: benzothiazole, benzimidazole, 3H-indolyl, indolyl, indazoyl, purinyl, quinolizinyl, isoquinolyl, quinolyl, phthalizinyl, naphthyridinyl, quinazolinyl, cinnolinyl, isothiazolyl, quinoxalinyl indolizinyl, isoindolyl, benzothienyl, benzofuranyl, isobenzofuranyl, and chromenyl moieties.

As used herein, the term "arylene" refers to a divalent all-carbon monocyclic or fused ring polycyclic (i.e., rings which share adjacent pairs of carbon atoms) Ar groups in which one or more of the rings has a completely conjugated pi-electron system. A "heteroarylene" group refers to a divalent monocyclic or fused ring group having in the ring(s) one or more atoms selected from the group consisting of nitrogen, oxygen and sulfur; in addition, at least one of the rings has a completely conjugated pi-electron system.

The term "heteroatom" as used herein refers to non-carbon, non-hydrogen atoms such as N, O, and S.

The Ar group may also be optionally substituted by replacement of one or more hydrogen atoms by another chemical moiety. Preferred substituents include $C_{1-6}$ alkyl straight or branched (e.g. isopropyl) chain, halogen, trihalomethyl, alkoxy, $NO_2$, $NH_2$, OH, —COOR', where R' is H or lower alkyl, $CH_2OH$, and $CONH_2$. Substitution of the Ar group also provides an attractive point for a linkage to which one or more additional polymeric moieties (e.g., polyalkylene oxide moieties) may be attached to the cross-linker.

As used herein, the term "alkyl" refers to a saturated aliphatic hydrocarbon including straight chain and branched chain groups. Preferably, the alkyl group has 1 to 20 carbon atoms. More preferably, it is a medium alkyl (having 1 to 10 carbon atoms). Most preferably, it is a lower alkyl (having 1 to 4 carbon atoms). The alkyl group may be substituted or unsubstituted. An "alkoxy" group refers to both an —O-alkyl and an —O-cycloalkyl group; preferably an alkoxy group refers to a lower alkoxy, and most preferably methoxy or ethoxy.

Valeric Acid Esters

Valeric acid esters have the general formula:

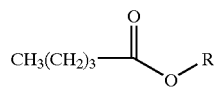

Functional Moieties

Designing a cross-linker involves selection of the functional moieties to be employed. The choice of functional moieties is entirely dependent upon the target sites available on the species to be crosslinked. Some species (e.g., proteins) may present a number of available sites for targeting (e.g., lysine ϵ-amino groups, cysteine sulfhydryl groups, glutamic acid carboxyl groups, etc.), and selection of a particular functional moiety may be made empirically in order to best preserve a biological property of interest (e.g., binding affinity of an antibody, catalytic activity of an enzyme, etc.)

1. Coupling Through Amine Groups

Imidoester and N-hydroxysuccinimidyl ("NHS") esters are typically employed as amine-specific functional moieties. NHS esters yield stable products upon reaction with primary or secondary amines. Coupling is efficient at physiological pH, and NHS-ester cross-linkers are more stable in solution than their imidate counterparts. Homobifunctional NHS-ester conjugations are commonly used to cross-link amine-containing proteins in either one-step or two-step reactions. Primary amines are the principle targets for NHS-esters. Accessible α-amine groups present on the N-termini of proteins react with NHS-esters to form amides. However, because α-amines on a protein are not always available, the reaction with side chains of amino acids become important. While five amino acids have nitrogen in their side chains, only the ϵ-amino group of lysine reacts significantly with NHS-esters. A covalent amide bond is formed when the NHS-ester cross-linking agent reacts with primary amines, releasing N-hydroxysuccinimide.

2. Coupling Through Sulfhydryl Groups

Maleimides, alkyl and aryl halides, α-haloacyls, and pyridyl disulfides are typically employed as sulfhydryl-specific functional moieties. The maleimide group is specific for sulfhydryl groups when the pH of the reaction mixture is kept between pH 6.5 and 7.5. At pH 7, the reaction of the maleimides with sulfhydryls is 1000-fold faster than with amines. Maleimides do not react with tyrosines, histidines or methionines. When free sulfhydryls are not present in sufficient quantities, they can often be generated by reduction of available disulfide bonds.

3. Coupling Through Carboxyl Groups

Carbodiimides couple carboxyls to primary amines or hydrazides, resulting in formation of amide or hydrazone bonds. Carbodiimides are unlike other conjugation reactions in that no cross-bridge is formed between the carbodiimide and the molecules being coupled; rather, a peptide bond is formed between an available carboxyl group and an available amine group. Carboxy termini of proteins can be targeted, as well as glutamic and aspartic acid side chains. In the presence of excess cross-linker, polymerization may occur because proteins contain both carboxyls and amines. No cross-bridge is formed, and the amide bond is the same as a peptide bond, so reversal of the cross-linking is impossible without destruction of the protein.

4. Nonselective Labeling

A photoaffinity reagent is a compound that is chemically inert but becomes reactive when exposed to ultraviolet or visible light. Arylazides are photoaffinity reagents that are photolyzed at wavelengths between 250–460 nm, forming a reactive aryl nitrene. The aryl nitrene reacts nonselectively to form a covalent bond. Reducing agents must be used with caution because they can reduce the azido group.

5. Arginine Specific Cross-linkers

Glyoxals are useful compounds for targeting the guanidinyl portion of arginine residues. Glyoxals will target arginines at mildly alkaline pH. There is some cross-reactivity (the greatest at higher pH) with lysines.

6. Carbonyl Specific Cross-Linkers

Carbonyls (aldehydes and ketones) react with amines and hydrazides at pH 5–7. The reaction with hydrazides is faster than with amines, making this useful for site-specific cross-linking. Carbonyls do not readily exist in proteins; however, mild oxidation of sugar moieties using sodium metaperiodate will convert vicinal hydroxyls to aldehydes or ketones.

Polymeric Moieties

The polymer substances included in the cross-linkers are preferably poly(alkylene oxides). As used herein, the term "alkylene oxide" refers to the structure, —X—O—, where X is an alkylene moiety covalently linked to oxygen O; thus poly(alkylene oxide) refers to the structure —(X—O—)$_m$—. It is preferred that the poly(alkylene oxide) polymer be a nonbranched homopolymer (i.e., a polymer of the structure —((CH$_2$)$_n$—O—)$_m$)— in which n does not vary) such as poly(ethylene oxide) derived from ethylene glycol. Alternative polymers such as other polyalkylene oxide homopolymers (e.g., methylene oxide, propylene oxide, isopropylene oxide, and butylene oxide polymers) and co-polymers or block co-polymers of poly(alkylene oxides) may also be used. In those aspects of the invention where PEG-based polymers are used, it is preferred that they have average molecular weights of from about 1,000 to about 25,000. Average molecular weights of about 2,000 to 5,000 are preferred and average molecular weights of from about 3,000 to about 3,500 are especially preferred. Molar equivalent amounts of the other alkylene oxides may be determined readily by those of ordinary skill in the art to arrive at preferred average molecular weights for other homopolymers and copolymers.

Average molecular weights of the present invention are measured using the "number-average" method. In a mixture of polymer molecules with different molecular weights in which the number of molecules having a particular molecular weight, $M_i$, is given by $N_i$, the "number-average" probability of a given mass being present is $$P_i = \frac{N_i}{\sum_{j=0}^{\infty} N_j}$$

and the number-average molecular weight is given by the formula $$\overline{M_n} = \sum_{i=0}^{\infty} \left( \frac{N_i}{\sum_{j=0}^{\infty} N_j} \right) M_i = \frac{\sum_{i=0}^{\infty} N_i M_i}{\sum_{j=0}^{\infty} N_j}$$

The number average is the simple arithmetic mean, representing the total weight of the molecules present divided by the total number of molecules. The number-average molecular weight of a polymer may be measured by vapor pressure osmometry using methods and apparatuses well known to those of skill in the art.

Alternative polymeric substances which may be used in place of poly(alkylene oxides) include materials such as dextran, polyvinyl pyrrolidones, polysaccharides, starches, polyvinyl alcohols, polyacryl amides or other similar polymers. Those of ordinary skill in the art will realize that the foregoing is merely illustrative and not intended to restrict the type of non-antigenic polymeric substances suitable for use herein.

The polymers are preferably activated in order to affect the desired linkages. By "activation," it is understood by those of ordinary skill in the art that the polymer is functionalized to directly or indirectly attach to a desired functional moiety as described herein.

Indirect Linkages to Functional Moieties

As described herein, a first functional moiety is directly or indirectly covalently linked to the aryl (or heteroaryl) portion of the N-aryl carbamic acid ester at one terminus of a polymeric moiety, and a second functional moiety is directly or indirectly covalently linked to another terminus of the polymeric moiety of the bifunctional cross-linkers described herein. The following exemplary molecule provides an example of each type of linkage:

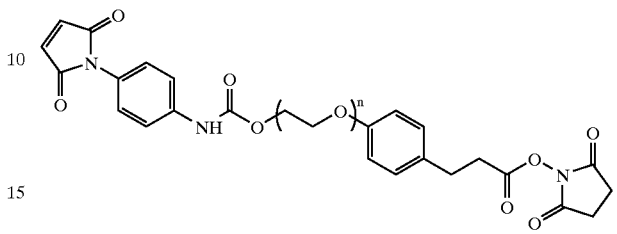

The term "directly covalently linked" indicates that no additional linkage chemistry is present between the functional moiety and the group on the N-aryl carbamic acid ester, or polymeric moiety terminus, to which the functional moiety is bound. In the exemplary molecule, a maleimide group is directly covalently linked at the para position to the phenyl portion of the N-phenyl carbamic acid ester. The term "indirectly covalently linked" indicates that some additional linkage chemistry is present. In the exemplary molecule, an N-hydroxy succinimide ester is linked via a phenylethyl group to a terminus of the polymeric moiety. Thus, the exemplary molecule comprises two "activated" ester linkages flanking the poly(ethylene oxide) core. Indirect linkages of the present invention may be from about 1 to 30 atoms, usually 1 to 15 atoms, where the atoms include C, N, O, S, P, etc., and will generally have from about 1 to 12 carbon atoms and from about 0 to 8, and usually 0 to 6, heteroatoms. The number of atoms referred to above are exclusive of hydrogen. In preferred embodiments, the indirect linkage chemistry is used to incorporate one or more aryl or heteroaryl ring structures into the molecule (in addition to that provided in the N-aryl carbamic acid ester).

Applications for Use of Cross-Linkers

1. Cell Surface Cross-Linking

To ensure cell-surface specific cross-linking for identification of surface receptors or their ligands, it is preferred to use membrane-impermeable cross-linkers. In the past, researchers used water-insoluble cross-linkers and carefully controlled the amount of cross-linker and the cross-linking duration. This prevented penetration of the membrane by the cross-linker and subsequent reaction with membrane proteins. Many references cite the use of membrane-permeable cross-linkers for cell surface cross-linking.

2. Subunit Cross-Linking and Protein Structural Studies

Cross-linkers can be used to study the structure and composition of proteins in biological samples. Some proteins are difficult to study because they exist in different conformations under varying pH or salt conditions. One way to avoid conformational changes is to cross-link the subunits together. Amine-, carboxyl- or sulfhydryl-reactive reagents are employed for identification of particular amino acids or for the determination of the number, location and size of subunits in a protein. Short-to-medium spacer arm cross-linkers are typically selected when intramolecular cross-linking is performed. If the spacer arm is too long, intermolecular cross-linking can occur.

3. Intermolecular Cross-Linking for the Study of Protein Interactions and Associations Cross-linkers are widely used for identification of near-neighbor protein relationships, ligand-receptor identification and interactions, and enzyme substrate orientations. The cross-linkers chosen for these applications are usually longer than those used for subunit cross-linking. Homobifunctional, amine-reactive NHS-esters or imidates and heterobifunctional, amine-reactive, photoactivatable phenyl azides are the most commonly-used cross-linkers for these procedures. Occasionally, a sulfhydryl- and amine-reactive cross-linker may be employed if one of the two proteins or molecules is know to contain sulthydryls. Cleavable or noncleavable cross-linkers are typically used. Because the distances between two molecules are not always known, the optimum length of the spacer arm of the cross-linker may be determined by the use of a panel of similar cross-linkers with different lengths. NHS-ester, phenylazides are very useful for this type of cross-linking because they usually result in some successful, if not efficient, cross-linking.

Cross-linkers can be used to determine whether a particular protein is located on the surface or the integral part of the membrane. These studies are possible because water-soluble cross-linkers are membrane-impermeable, while water-insoluble cross-linkers are membrane permeable.

4. Cell Membrane Structural Studies

Cell membrane structural studies require reagents of varying hydrophobicity to determine the location and the environment within a cell's lipid bilayer. Fluorescent tags are used to locate proteins, lipids or other molecules inside and outside the membrane. Various cross-linkers with differing spacer arm lengths can be used to cross-link proteins to associated molecules within the membrane to determine the distance between molecules. Successful cross-linking with shorter cross-linkers is a strong indication that two molecules are interacting in some manner. Failure to obtain cross-linking with a panel of shorter cross-linkers, while obtaining conjugation with the use of longer reagents, generally indicates that the molecules are located in the same part of the membrane but are not interacting. Homobifunctional NHS-esters, imidates or heterobifunctional NHS-esters, photoactivatable, phenyl azides are commonly used for these procedures.

5. Immunotoxins

Specific antibodies can be covalently linked to toxic molecules and then used to target antigens on cells. Often these antibodies are specific for tumor associated antigens. Immunotoxins are brought into the cell by surface antigens and, once internalized, they proceed to kill the cell by ribosome inactivation or other means. The type of cross-linker used to make an immunotoxin can affect its ability to locate and kill the appropriate cells. For immunotoxins to be effective, the conjugate must be stable in vivo. In addition, once the immunotoxin reaches its target, it is important that the antibody be separable from the toxin to allow the toxin to kill the cell. Thiol-cleavable, disulfide-containing conjugates have been shown to be more cytotoxic to tumor cells than noncleavable conjugates of ricin A immunotoxins. Cells are able to break the disulfide bond in the cross-linker, allowing the release of the toxin within the targeted cell.

6. Carrier Protein-Hapten/Peptide/Polypeptide Conjugates for Use as Immunogens

Numerous companies offer commercially available products in this area of immunological research. There are many cross-linkers used for the production of these conjugates, and the best choice is dependent on the reactive groups present on the hapten and the ability of the hapten carrier conjugate to function successfully as an immunogen after its injection. Carbodiimides are good choices for producing peptide carrier conjugates because both proteins and peptides usually contain several carboxyls and primary amines.

Other heterobifunctional cross-linkers can also be used to make immunogen conjugates. Often peptides are synthesized with terminal cysteines to allow for their attachment to supports or to carrier proteins through a part of the molecule that is not important for activity or recognition. Sulfhydryl-reactive, heterobifunctional cross-linkers can be coupled to carrier proteins through their other functional group and then can be linked to peptides through terminal cysteines. This method can be very efficient and yield an immunogen that is capable of eliciting a good response upon injection.

7. Solid-Phase Immobilization

Proteins, peptides and other molecules can be immobilized on solid-phase matrices for use as affinity supports or for sample analysis. The term "solid phase" as used herein refers to a wide variety of materials including solids, semi-solids, gels, films, membranes, meshes, felts, composites, particles, papers and the like typically used by those of skill in the art to sequester molecules. The solid phase can be nonporous or porous. Suitable solid phases include those developed and/or used as solid phases in solid phase binding assays. See, e.g., chapter 9 of *Immunoassay*, E. P. Dianiandis and T. K. Christopoulos eds., Academic Press: New York, 1996, hereby incorporated by reference. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997, 1998; Kessler et al., Agnew. Chem. Int. Ed. 40: 165, 2001; Smith et al., J. Comb. Med. 1: 326, 1999; Orain et al., Tetrahedron Lett. 42: 515, 2001; Papanikos et al., J. Am. Chem. Soc. 123: 2176, 2001; Gottschling et al., Bioorg. Med. Chem. Lett. 11: 2997, 2001.

Surfaces such as those described above may be modified to provide linkage sites, for example by bromoacetylation, silation, addition of amino groups using nitric acid, and attachment of intermediary proteins, dendrimers and/or star polymers. This list is not meant to be limiting, and any method known to those of skill in the art may be employed.

8. Detectable Label Conjugates

One of the most widely used applications for cross-linkers is the production of protein-protein conjugates. Biological assays require methods for detection, and one of the most common methods for quantitation of results is to conjugate an enzyme, fluorophore or other molecule to a protein or nucleic acid that has affinity for one of the components in the biological system being studied. Antibody-enzyme conjugates (primary or secondary antibodies) are among the most common protein-protein conjugates used. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Particularly preferred detectable labels are fluorescent latex particles such as those described in U.S. Pat. Nos. 5,763,189, 6,238,931, and 6,251,687; and International Publication WO95/08772, each of which is hereby incorporated by reference in its entirety. Exemplary conjugation to such particles is described hereinafter.

Use of Cross-Linkers in Receptor Binding Assays

The cross-linkers of the present invention may be advantageously used to covalently link solid phases or detectable labels to proteins, polypeptides, antibodies, small molecules, nucleic acids, oligosaccharides, polysaccharides, cyclic polypeptides, peptidomimetics, and aptamers. This list is not meant to be limiting. In preferred embodiments, these conjugates are used in receptor binding assays. Receptor binding assays include any assay in which a signal is dependent upon specific binding of an analyte to a cognate receptor, and include immunoassays, ligand-receptor assays, and nucleic acid hybridization assays.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3$^{rd}$ Edition, W. E. Paul, ed., Raven Press, N.Y. (1993); Wilson (1994) *J. Immunol. Methods* 175:267–273; Yarmush (1992) *J. Biochem. Biophys. Methods* 25:85–97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Single chain antibodies are also included by reference in the term "antibody."

The term "polypeptide" as used herein refers to a molecule having a sequence of amino acids linked by peptide bonds. This term includes proteins, fusion proteins, oligopeptides, cyclic peptides, and polypeptide derivatives. Antibodies and antibody derivatives are discussed above in a separate section, but antibodies and antibody derivatives are, for purposes of the invention, treated as a subclass of the polypeptides and derivatives. The term protein refers to a polypeptide that is isolated from a natural source, or produced from an isolated cDNA using recombinant DNA technology, and that has a sequence of amino acids having a length of at least about 200 amino acids.

The term "nucleic acids" as used herein shall be generic to polydeoxyribonucleotides (containing 2'-deoxy-D-ribose or modified forms thereof), to polyribonucleotides (containing D-ribose or modified forms thereof), and to any other type of polynucleotide which is an N-glycoside of purine or pyrimidine bases, or modified purine or pyrimidine bases.

The term "aptamer" as used herein is a single-stranded or double-stranded oligodeoxyribonucleotide, oligoribonucleotide or modified derivatives that specifically bind and alter the biological function of a target molecule. The target molecule is defined as a protein, peptide and derivatives thereof. The aptamer is capable of binding the target molecule under physiological conditions. An aptamer effect is distinguished from an antisense effect in that the aptameric effects are induced by binding to the protein, peptide and derivative thereof and are not induced by interaction or binding under physiological conditions with nucleic acid.

The term "polysaccharide" as used herein refers to a molecule comprising more than 10 glycosidically linked monosaccharide residues, while the term "oligosaccharide" refers to a molecule comprising from 2–10 glycosidically linked monosaccharide residues.

The term "small molecule" includes any molecule having a molecular weight less than about 5,000 daltons (Da), preferably less than about 2,500 Da, more preferably less than 1,000 Da, most preferably less than about 500 Da.

The presence or amount of an analyte is generally determined using antibodies specific for each marker and detecting specific binding. Any suitable immunoassay may be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

Numerous methods and devices are well known to the skilled artisan for the practice of receptor binding assays. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety, including all tables, figures and claims. These devices and methods can utilize detectably labeled molecules and antibody solid phases in various sandwich, competitive, or non-competitive assay formats, to generate a signal that is related to the presence or amount of an analyte of interest. One skilled in the art also recognizes that robotic instrumentation including but not limited to Beckman Access, Abbott AxSym, Roche ElecSys, Dade Behring Stratus systems are among the immunoassay analyzers that are capable of performing such immunoassays. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. In such an assay the cross-linkers of the present invention could be used to increase the mass of material binding to the assay surface for detection.

In its simplest form, an assay device may be a solid surface comprising receptor(s) that specifically bind one or more analytes of interest. For example, antibodies may be immobilized onto a variety of solid supports, such as magnetic or chromatographic matrix particles, the surface of an assay plate (such as microtiter wells), pieces of a solid substrate material or membrane (such as plastic, nylon, paper), and the like using the cross-linkers of the present invention.

The analysis of a plurality of analytes may be carried out separately or simultaneously with one test sample. For separate or sequential assay of markers, suitable apparatuses include clinical laboratory analyzers such as the ElecSys (Roche), the AxSym (Abbott), the Access (Beckman), the ADVIA® CENTAUR® (Bayer) immunoassay systems, the NICHOLS ADVANTAGE® (Nichols Institute) immunoassay system, etc. Preferred apparatuses or protein chips perform simultaneous assays of a plurality of analytes on a single surface. Particularly useful physical formats comprise surfaces having a plurality of discrete, addressable locations for the detection of a plurality of different analytes. Such formats include protein microarrays, or "protein chips" (see, e.g., Ng and Ilag, *J. Cell Mol. Med.* 6: 329–340 (2002)) and certain capillary devices (see, e.g., U.S. Pat. No. 6,019,944). In these embodiments, each discrete surface location may comprise antibodies to immobilize one or more analyte(s) (e.g., a marker) for detection at each location. Surfaces may alternatively comprise one or more discrete particles (e.g., microparticles or nanoparticles) immobilized at discrete locations of a surface, where the microparticles comprise antibodies to immobilize one analyte (e.g., a marker) for detection.

EXAMPLES

The following examples serve to illustrate the present invention. These examples are in no way intended to limit the scope of the invention.

Example 1

Preparation of NHS—N-aryl Carbamic Acid Ester-Polyethylene Oxide-Valeric Acid-Maleimide (NCVM) Bifunctional Linker A solution of 20 mmol poly(ethylene glycol) having an average molecular weight of 3400 in 300 mL toluene was refluxed with stirring, and the azeotroped water collected using a Dean-Stark trap and discarded. After about 90 mL of distillate was collected and discarded in this manner, the remaining contents were cooled to about 30° C. and treated with 40 mmol sodium hydride. After 1 hour, 40 mmol ethyl-5-bromovalerate was added with rapid stirring. The solution was stirred overnight, at which time a solid precipitate had formed. The solid was heated to a liquid and evaporated to dryness.

The remaining solid residue was dissolved in 150 mL methylene chloride, re-evaporated to dryness, and 100 mL 1 N NaOH added to the remaining solid residue. The mixture was swirled to dissolve, and left at room temperature overnight. The resulting solution was acidified to pH<2 by the addition of about 17 mL 6N HCl. 20 g NaCl was dissolved into the acidified solution, followed by extraction with 3×150 mL methylene chloride. 20 g anhydrous $MgSO_4$ was added to the combined organic partitions, and the resulting solution stirred for 72 hours.

The resulting mixture was filtered, and the retained $MgSO_4$ washed with 100 mL methylene chloride. The filtrate was evaporated to leave a white solid, which was washed with 300 mL diethyl ether by stirring for 2 hours followed by collection of the solid by filtration. This solid was again washed with 200 mL diethyl ether, collected, and dried under vacuum to yield a mixture of poly(ethylene glycol)-valeric acid having the formula $HO(CH_2CH_2O)_n(CH_2)_4C(O)OH$. The product was purified from unreacted starting materials and unwanted reaction products by anion exchange chromatography on DEAE sephadex.

To activate the hydroxyl group, the poly(ethylene glycol)-valeric acid (0.37 mmol) was stirred in 5 mL acetonitrile, and 0.93 mmol N-[p-Maleiomidophenyl] isocyanate (PMPI) was added. Stirring was continued overnight under argon at 60° C. The solvent was then evaporated and the resulting residue redissolved in 15 mL $H_2O$. The solution was centrifuged to remove residual solids, and the supernatant collected and evaporated. The residue was redissolved in methylene chloride and again evaporated to provide a solid residue.

The resulting solids were dissolved in 20 ml of hot isopropyl alcohol and allowed to cool with stirring. The solution was allowed to stand at room temperature for 4 hours, and then at 4° C. overnight. The solids were collected by filtration, washed with 10 mL cold isopropyl alcohol, 20 mL diethyl ether, and dried under vacuum.

To activate the valeric acid group, the maleimido-poly (ethylene glycol) valeric acid (0.33 mmol) was dissolved in 9 mL acetonitrile, and 0.373 mmol N-hydroxysuccinimide, followed by 0.405 mmol N,N'-dicyclohexylcarbodiimide (from a 1 M solution in methylene chloride) were added. The resulting solution was held overnight at room temperature under argon. The solution was evaporated, and the residue redissolved in 10 mL methylene chloride. The mixture was filtered to remove residual solids, and the filtrate evaporated. The resulting residue was treated with 20 mL diethyl ether, filtered, and the solids washed with ether to provide the NCVM linker as a solid:

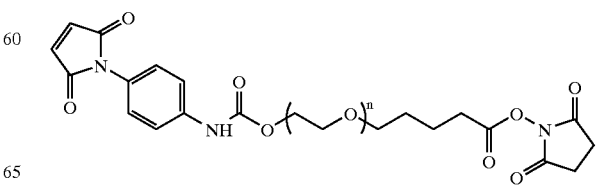

Example 2

Preparation of NHS—N-aryl Carbamic Acid Ester-Polyethylene Oxide-Maleimide (NCAM) Bifunctional Linker A solution of 40 mmol poly(ethylene glycol) having an average molecular weight of 3400 in 300 mL toluene was refluxed with stirring, and the azeotroped water collected using a Dean and Stark trap and discarded. After about 250 mL of distillate was collected and discarded in this manner, the remaining contents were evaporated and solid triphenyl phosphine (23.88 mmol) and methyl-4-hydroxyphenylpropionate (23.88 mmol) added to the residue. The solids were dissolved in 205 mL tetrahydrofuran, and 23.88 mmol diisopropylazodicarboxylate was added with stirring. The solution was stirred overnight under argon. The volume of the solution was reduced by about 50% by evaporation, and 200 mL diethyl ether was added. The resulting solution was poured into 1.3 L diethyl ether, and brought to a final volume of 1.8 L. The resulting solid was collected, washed with 3×100 mL diethyl ether and dried under vacuum to yield a poly(ethylene glycol)-phenylpropionic acid methyl ester having the formula $HO(CH_2CH_2O)_nC_6H_4(CH_2)_2C(O)OCH_3$.

The poly(ethylene glycol) phenyl propionic acid ester (19.8 mmol) was dissolved in 250 mL water, and 198 mmol solid NaOH added. The mixture was stirred at room temperature overnight. The resulting solution was acidified to pH 2.4 by the addition of 11.6N HCl. The solvent was evaporated, and the residue dissolved in 400 mL methylene chloride, and anhydrous $MgSO_4$ was added and the resulting solution stirred overnight. The solvent was again evaporated, and the residue dissolved in 100 mL methylene chloride. 100 mL diethyl ether was added. The resulting solution was poured into 1.4 L diethyl ether, and brought to a final volume of 1.8 L. The resulting solid was collected, washed with 3×100 mL diethyl ether and dried under vacuum to yield a poly(ethylene glycol) phenyl propionic acid having the formula $HO(CH_2CH_2O)_nC_6H_4(CH_2)_2C(O)OH$. The product was purified from unreacted starting materials and unwanted reaction products by anion exchange chromatography on DEAE sephadex.

To activate the hydroxyl group, the poly(ethylene glycol) phenyl propionic acid (0.1.12 mmol) was stirred in 20 mL acetonitrile, and 2.8 mmol N-[p-Maleiomidophenyl] isocyanate (PMPI) was added. Stirring was continued overnight under argon at 60° C. The solvent was then evaporated and the resulting residue redissolved in 40 mL $H_2O$. The solution was centrifuged to remove residual solids, and the supernatant collected and evaporated. The residue was redissolved in 40 mL methylene chloride and again evaporated to provide a solid residue.

The resulting solids were dissolved in 50 ml of hot isopropyl alcohol and allowed to cool with stirring. The solution was allowed to stand at room temperature for 4 hours, and then at 4° C. overnight. The solids were collected by filtration, washed with 10 mL cold isopropyl alcohol, 20 mL diethyl ether, and dried under vacuum.

To activate the propionic acid group, the maleimido-poly(ethylene glycol) propionic acid (1.0 mmol) was dissolved in 25 mL acetonitrile, and 1.13 mmol N-hydroxysuccinimide, followed by 1.2 mmol N,N'-dicyclohexylcarbodiimide (from a 1 M solution in methylene chloride) were added. The resulting solution was held overnight at room temperature under argon. The solution was evaporated, and the residue redissolved in 10 mL acetonitrile. The mixture was filtered to remove residual solids, and the filtrate added to 150 mL diethyl ether. The resulting precipitate was washed with 2×25 mL diethyl ether collected to provide the NCAM linker as a solid:

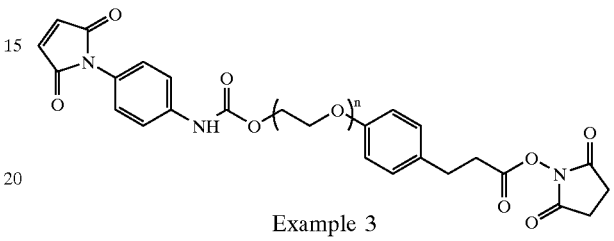

Example 3

Preparation of NHS-Polyethylene Oxide-Valeric Acid Ester-Maleimide (NVAM) Bifunctional Linker A solution of 20 mmol poly(ethylene glycol) having an average molecular weight of 3400 in 300 mL toluene was refluxed with stirring, and the azeotroped water collected using a Dean-Stark trap and discarded. After about 90 mL of distillate was collected and discarded in this manner, the remaining contents were cooled to about 30° C. and treated with 40 mmol sodium hydride. After 1 hour, 40 mmol ethyl-5-bromovalerate was added with rapid stirring. The solution was stirred overnight, at which time a solid precipitate had formed. The solid was heated to a liquid and evaporated to dryness.

The remaining solid residue was dissolved in 150 mL methylene chloride, re-evaporated to dryness, and 100 mL 1 N NaOH added to the remaining solid residue. The mixture was swirled to dissolve, and left at room temperature overnight. The resulting solution was acidified to pH<2 by the addition of about 17 mL 11.6N HCl. 20 g NaCl was dissolved into the acidified solution, followed by extraction with 3×150 mL methylene chloride. 20 g anhydrous $MgSO_4$ was added to the combined organic partitions, and the resulting solution stirred for 72 hours.

The resulting mixture was filtered, and the retained $MgSO_4$ washed with 100 mL methylene chloride. The filtrate was evaporated to leave a white solid, which was washed with 300 mL diethyl ether by stirring for 2 hours followed by collection of the solid by filtration. This solid was again washed with 200 mL diethyl ether, collected, and dried under vacuum to yield a poly(ethylene glycol)-valeric acid having the formula $HO(CH_2CH_2O)_n(CH_2)_4C(O)OH$. The product was purified from unreacted starting materials and unwanted reaction products by anion exchange chromatography on DEAE sephadex.

The poly(ethylene glycol)-valeric acid (1.15 mmol) was stirred in 50 mL methanol in a dry ice/isopropyl alcohol bath, and 100 mmol thionyl chloride was added dropwise. The mixture was brought to room temperature and stirred overnight. The solution was evaporated to leave a white solid, which was then dissolved in 20 mL methylene chloride. The solution was treated with 20 mL diethyl ether, and added to 200 mL diethyl ether, with rapid stirring for 1 hour. The resulting precipitate was collected by filtration, washed with 100 mL diethyl ether, and dried under vacuum to yield a poly(ethylene glycol) valeric acid methyl ester having the formula $HO(CH_2CH_2O)_n(CH_2)_4C(O)OCH_3$.

The poly(ethylene glycol)-valeric acid methyl ester (1.12 mmol), together with triphenylphosphine (6.75 mmol) was stirred in 20 mL tetrahydrofuran, and 13.5 mmol hydrazoic acid in benzene was added. To this solution, 6.62 mmol diisopropylazodicarboxylate was added under an argon atmosphere, and allowed to stir overnight. An additional 2.25 mmol triphenylphosphine and 4.5 mmol hydrazoic acid in benzene were added, and the resulting solution was stirred at room temperature for 3 hours. 20 mL diethyl ether was added, and the entire contents added to 350 mL diethyl ether with rapid stirring. The resulting precipitate was collected by filtration, washed with 2×50 mL diethyl ether, and dried under vacuum to yield an azido poly(ethylene glycol)-valeric acid methyl ester having the formula $N_3(CH_2CH_2O)_n(CH_2)_4C(O)OCH_3$. The azido compound (1.1 mmol) was reduced to the corresponding amino compound by hydrogenation overnight in methanol containing 10% Pd/C (palladium on carbon support). The solution was filtered and evaporated to leave an amino poly(ethylene glycol)-valeric acid methyl ester having the formula $H_2N(CH_2CH_2O)_n(CH_2)_4C(O)OCH_3$.

The amino poly(ethylene glycol)-valeric acid methyl ester (1.1. mmol) was dissolved in 10 mL 1 N NaOH, held at room temperature overnight, and acidified to pH 2 with 6N HCl. 2 g NaCl was added, and the resulting solution filtered to remove residual palladium catalyst. The solution was extracted 3× with 20 mL methylene chloride, and $MgSO_4$ was added to the combined organic phases, followed by stirring at room temperature overnight. The solution was evaporated, and the resulting solid product suspended in 30 mL diethyl ether with stirring for 2 hours. The solid product was collected by filtration, washed with 30 mL diethyl ether, and dried under vacuum to leave an amino poly(ethylene glycol) valeric acid salt having the formula $H_2N(CH_2CH_2O)_n (CH_2)_4C(O)OH\cdot HCl$.

The amino group on this compound was activated using N-[β-maleimidopropyloxy]succinimide ester (BMPS) by dissolving the amino poly(ethylene glycol) valeric acid (0.57 mmol) in 10 mL acetonitrile, and adding 0.62 mmol BMPS. The resulting solution was treated with 0.57 mmol N,N-Diisopropylethylamine and stirred at room temperature overnight. The valeric acid group on this compound was then activated by adding 1.132 mmol N-hydroxysuccinimide, followed by 1.13 mmol N,N'-dicyclohexylcarbodiimide (from a 1M solution in methylene chloride) and stirring overnight at room temperature under argon. The solution is filtered, and the filtrate evaporated to yield a solid product. The solid is dissolved in 5 mL methylene chloride, 5 mL diethyl ether is added, and the solution is added dropwise to 100 mL diethyl ether with rapid stirring to precipitate the NVAM linker as a solid:

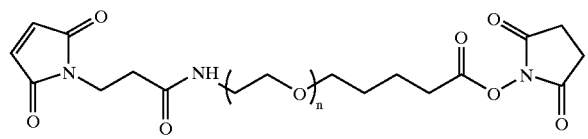

Example 4

Preparation of Antibody-Solid Phase Conjugates

Bovine serum albumin ("BSA") and polystyrene latex particles (Interfacial Dynamics) are incubated at 25° C. for 30 minutes at 1–10 mg BSA per mL of latex slurry at 1–10% solids in 25 mM citrate buffer, pH approximately 4. The solution is then brought to approximately neutral pH with 150 mM potassium phosphate/30 mM potassium borate, and incubated for an additional 2 hours at 25° C. The suspension is washed three times by resuspension in 50 mM potassium phosphate/10 mM potassium borate/150 mM sodium chloride at approximately neutral pH followed by centrifugation.

The N-hydroxysuccinimide/maleimide bifunctional poly(ethylene glycol) crosslinker is added at 5–500 mg/mL in deionized water to the BSA-latex particles at 1–10% solids. The crosslinker is incubated with the BSA-latex particles at room temperature for 2 hours. Excess crosslinker is removed by centrifugation and resuspension in PBS of the now maleimide-functionalized BSA-latex particles.

Concurrently, a 1–10 mg/mL solution of cysteinylated Fab' fragments in 50 mM potassium phosphate/10 mM potassium borate/150 mM sodium chloride at approximately neutral pH are reduced with DTT for 30 minutes at 25° C. Excess DTT is removed by dialysis against this same buffer.

The maleimide-functionalized BSA-latex particles are added to a solution containing 0.2–10 mg/ml of the Fab' fragments in the presence of 0.1 mM EDTA, and the mixture is incubated at room temperature overnight. The reaction is stopped by addition of 02 mM β-mercaptoethanol and 6 mM N-(hydroxyethyl)maleimide for 30 minutes each. The antibody-conjugated latex particles is purified by centrifugation and resuspension in PBS.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of conjugating a first species selected from the group consisting of a protein, a polypeptide, an antibody, a nucleic acid, a small molecule, an aptamer, and a carbohydrate, to a second species selected from the group consisting of a detectable label, a solid phase, a protein, a polypeptide, an antibody, a nucleic acid, a small molecule, an aptamer, and a carbohydrate, the method comprising:

contacting said first and second species with a crosslinker of the formula:

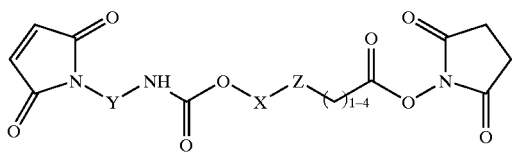

wherein X is (alkylene oxide)$_n$;

n is between about 40 to about 450; and

Y and Z are independently arylene or heteroarylene units having 5 or 6 ring atoms, optionally substituted with from 1 to 4 substituents independently selected from the group consisting of $C_{1-6}$ alkyl straight or branched chain, halogen, trihalomethyl, $C_{1-6}$ alkoxy, —$NO_2$, —$NH_2$, —OH, —COOR', where R' is H or lower alkyl, —$CH_2OH$, —$CONH_2$, and a linkage to a poly(alkylene oxide) moiety, wherein Z is optionally present;

under conditions selected to conjugate said first species to said second species, wherein one of the first or second species becomes covalently bound to said crosslinker through a moiety reactive with an N-hydroxysuccinimide functional group, and the other of the first or second species becomes covalently bound to said crosslinker through a moiety reactive with a maleimide functional group wherein the conjugating step comprises (i) covalent binding of the crosslinker to the first or second species through a moiety reactive with a first functional group that is an N-hydroxysuccinimide or a maleimide functional group, to form a covalently bound crosslinker intermediate; (ii) removal of unreacted crosslinker from the covalently bound crosslinker intermediate; and (iii) covalent binding of the crosslinker to the other of the first or second species through a moiety reactive with a second functional group that is the other of the N-hydroxysuccinimide or maleimide functional group.

2. A method according to claim 1, wherein the crosslinker has the formula:

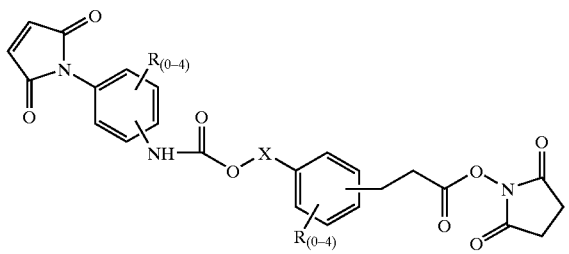

wherein X is (alkylene oxide)$_n$;

n is between about 40 to about 450; and each R is independently selected from the group consisting of $C_{1-6}$ alkyl straight or branched chain, halogen, trihalomethyl, $C_{1-6}$ alkoxy, $NO_2$, $NH_2$, OH, —COOR', where R' is H or lower alkyl, $CH_2OH$, $CONH_2$, and a linkage to a polyalkylene oxide moiety.

3. A method according to claim 1, wherein the (alkylene oxide)$_n$ group is a copolymer of two or more units selected from the group consisting of methylene oxide, ethylene oxide, propylene oxide, isopropylene oxide, and butylene oxide.

4. A method according to claim 1, wherein the (alkylene oxide)n group is a homopolymer of units selected from the group consisting of methylene oxide, ethylene oxide, propylene oxide, isopropylene oxide, and butylene oxide.

5. A method according to claim 1, wherein the crosslinker has the formula:

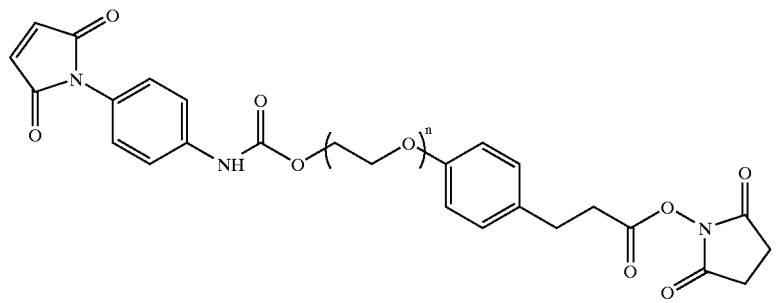

wherein n is between about 40 to about 450.

6. A method according to claim 5, wherein n is between 60 and 100.

7. A method according to claim 5, wherein n is between 70 and 90.

8. A method according to claim 5, wherein n averages about 77.

9. A method according to claim 1, wherein the conjugating step comprises (i) covalent binding of the crosslinker to the first or second species through a moiety reactive with an N-hydroxysuccinimide functional group to form a covalently bound crosslinker intermediate; (ii) removal of unreacted crosslinker from the covalently bound crosslinker intermediate; and (iii) covalent binding of the crosslinker to the other of the first or second species through a moiety reactive with a maleimide functional group.

10. A method according to claim 1, wherein the first or second species is an antibody.

11. A method according to claim 1, wherein the second species is a latex particle comprising a moiety reactive with a N-hydroxysuccinimide functional group or reactive with a maleimide functional group.

12. A method according to claim 1, wherein the second species is a solid phase modified to provide linkage sites for the crosslinker.

13. A method according to claim 12, wherein the second species is a latex particle, and the linkage sites are provided by an intermediary protein.

14. A method according to claim 1, wherein the first species is an antibody, and the second species is a solid phase comprising linkage sites for the crosslinker.

15. A method according to claim 14, wherein the second species is a latex particle comprising a moiety reactive with a N-hydroxysuccinimide functional group or reactive with a maleimide functional group.

16. A method according to claim 15, wherein the latex particle is covalently bound to the crosslinker through a moiety reactive with an N-hydroxysuccinimide functional group provided on an intermediary protein, and wherein the antibody is covalently bound through a moiety reactive with a maleimide functional group provided by cystenylation of the antibody.

* * * * *